United States Patent [19]

Colson et al.

[11] Patent Number: 4,469,791

[45] Date of Patent: Sep. 4, 1984

[54] GENETICALLY ENGINEERED MICROORGANISMS FOR MASSIVE PRODUCTION OF AMYLOLYTIC ENZYMES AND PROCESS FOR PREPARING SAME

[75] Inventors: Charles A. Colson; Pierre E. Cornelis, both of Dion-Valmont; Colette S. Digneffe, Rosieres; Corinne Walon, Wavre, all of Belgium

[73] Assignee: CPC International Inc., Englewood Cliffs, N.J.

[21] Appl. No.: 234,140

[22] Filed: Feb. 13, 1981

[30] Foreign Application Priority Data

Feb. 15, 1980 [GB] United Kingdom ................. 8005184
Apr. 10, 1980 [GB] United Kingdom ................. 8011842

[51] Int. Cl.$^3$ ...................... C12N 15/00; C12N 1/20; C12N 9/28; C12R 1/19
[52] U.S. Cl. ................................. 435/253; 435/172.3; 435/202; 435/317; 435/849; 435/839; 935/14; 935/29; 935/31; 935/73; 935/74
[58] Field of Search ................. 435/68, 201, 172, 317

[56] References Cited

U.S. PATENT DOCUMENTS 4,237,224  12/1980  Cohen et al. .......................... 435/68

FOREIGN PATENT DOCUMENTS

| 76480 | 6/1977 | Japan ................................... 435/172 |
| 52-76480 | 6/1977 | Japan . |
| 1521032 | 8/1978 | United Kingdom . |
| 1565190 | 4/1980 | United Kingdom . |
| 2031905 | 4/1980 | United Kingdom . |

OTHER PUBLICATIONS

Yoneda et al., Cloning of a Foreign Gene Coding for α Amylase in *Bacillus subtilis* Biochem Biophy Res. Com., vol. 91, 1979, pp. 1556–1564.

Shinomiya et al., Isolation of a *Bacillus subtilis* Transforment Producing Thermostable α-Amylase by DNA from a Thermophilic Bacteum Biochem Bioph. Res. Com., vol. 96, 1980, pp. 175–179.

Broda *Plasmids* 1979, Freeman and Co., San Francisco, pp. 5–23.

Lewin *Gene Expression,* 1977, John Wiley & Sons, New York, p. 269.

Timmis, et al., DNA Cloning and the Analysis of Plasmid Structure and Function, *Prog. Molec. Subcellular Biol.* 6, 1978, pp. 1–58.

Murray et al., Lamboid Phages that Simplify the Recovery of *in vitro* Recombinants, *Molec. Gen. Genet,* 150, 1977, pp. 53–61.

Hohn, Packaging Recombinant DNA Molecules into Bacteriophage Particle *in vitro, Proc. Natl. Acad. Sci. USA,* 74, 1977, pp. 3259–3263.

Nomura, et al., Construction of Transducing Phage p. 11, Containing Alpha-Amylase Structural Gene of *Bacillus subtilis,* Ag. Bio. Chem. 43,2637–43,2638, 79.

Yoneda, Increased Production of Extracellular Enzymes, *Applied and Environmental Microbiology,* 39, 274–276, 1980.

MacDonald, et al., *Nature,* Structure of a Family of Rat Amylase Genes, 287,117–287,122, (1980).

*Primary Examiner*—Jerome D. Goldberg
*Assistant Examiner*—K. S. McCowin

[57] ABSTRACT

Genetically engineered microorganisms are provided which contain recombinant DNA with an amylase coding gene. Improved yields of amylase enzymes are obtained by cultivating these microorganisms.

11 Claims, 7 Drawing Figures

GENETICALLY ENGINEERED MICROORGANISMS FOR MASSIVE PRODUCTION OF AMYLOLYTIC ENZYMES AND PROCESS FOR PREPARING SAME

FIELD OF THE INVENTION

This invention relates to the production of recombinant DNA (deoxyribonucleic acid) containing an amylase coding gene, and to the utilization of this DNA to produce microorganisms for the massive production of amylolytic enzymes.

BACKGROUND OF THE INVENTION

Large quantities of amylases are used industrially to carry out starch hydrolysis reactions, frequently referred to as enzymatic liquefaction and saccharification of starch. Such reactions are used to produce adhesives, sizings, maltodextrins, starch syrups of various compositions, maltose and dextrose. For industrial processes, it is particularly useful to have enzymes which are thermostable, which operate at selected pH ranges and which show resistance to heavy metal poisoning. Because of the commercial importance of amylases, there are great incentives to find low-cost sources for those enzymes having specific desired properties.

The amylases can be obtained from various microorganisms. It is known that these microorganisms contain genetic material which codes for the production of the enzymes by the organism. This genetic material is present in the form of DNA within the cell.

By techniques referred to as genetic engineering, it is possible to transfer a portion of the DNA from one organism to another. Attempts have been made to use these techniques to develop microorganisms which are amylase producers.

Two excellent reviews on the subject of genetic engineering are "DNA Cloning and the Analysis of Plasmid Structure and Function" by K. N. Timmis, S. N. Cohen and S. C. Cabello, *Prog. Molec. subcell Biol.*, 6, 1978, pp. 1–58, and "Lamboid Phages that Simplify the Recovery of in vitro Recombinants" by Noreen E. Murray, W. J. Brammar and K. Murray, *Molec. gen. Genet.*, 150, 1977, pp. 53–61. These reviews include many reports describing new, genetically modified microorganisms having valuable properties. Japanese patent publication No. SHO 52-76480 (published June 27, 1977, filed December 19, 1975 as SHO 50-150641) to Maruo, et al, discloses the manufacture of high-amylase producing strains of microorganisms by the in vivo techniques of mutagenesis, transduction and transformation to accumulate several genetic traits promoting amylase production in a Bacillus microorganism. These techniques, which do not comprise genetic engineering as herein defined, are limited to a single or a few closely related (genetically speaking) microorganisms. Also, these strains are not amenable to the gene amplification (e.g., by phage or plasmid) used in the instant invention for higher enzyme production.

In a recent article by Yuko Yoneda, Scott Graham and Frank E. Young, entitled "Cloning of a Foreign Gene Coding for alpha-Amylase in *Bacillus subtilis*", *Biochemical and Biophysical Research Communications*, 91, No. 4, pp. 1556–1564 (December 28, 1979), the authors describe the cloning of an alpha-amylase coding gene into a *Bacillus subtilis* (hereafter written *B. subtilis*) by bonding cleaved DNA of *Bacillus amyloliquefaciensH* with the DNA of the temperate phage phi 3T and subsequently transforming *B. subtilis* amylase-deficient cells. The authors do not show any evidence of amplification of the gene, with attendant massive production of the amylase enzyme, which is an important objective of the present invention.

SUMMARY OF THE INVENTION

In accordance with this invention, there is provided recombinant DNA consisting of phages and plasmids which contain an amylase or pullulanase gene. Also disclosed are genetically engineered microorganisms containing these phages and plasmids and their use to produce amylase and pullulanase enzymes.

BRIEF DESCRIPTION OF THE DRAWINGS

FIG. 3 shows the relationship between the known plasmid vector pC194, FIG. 3(*a*); the new plasmid pCP 2.3, FIG. 3(*b*), formed by ligating DNA fragments obtained by cutting pCP 2 with Eco RI and Hind III; and the new plasmid pCH 1, FIG. 3(*c*), formed by inserting plasmid pC194 into pCP 2.3.

In all of the figures, the donor DNA is indicated by a heavy line.

DETAILED DESCRIPTION OF THE INVENTION

Although the term "genetic engineering" is frequently used to describe a large number of techniques for the artificial modification of the genetic information of an organism, throughout the specification and claims it is employed only in reference to the in vitro technique of forming recombinant DNA's from a donor microorganism and a suitable vector, selecting on the basis of the desired genetic information, and introducing the selected DNA into a suitable microorganism (host microorganism) whereby the desired (foreign) genetic information becomes part of the genetic complement of the host. The term "genetically engineered microorganism", as used throughout the specification and claims, means a microorganism prepared by this technique.

The terms "amylase" and "amylolytic enzyme" are synonymous, and as used throughout the specification and claims refer broadly to those enzymes capable of catalyzing the hydrolysis of starch, such as alpha-amylase, beta-amylase, iso-amylase (including the alpha-1,6-glucosidases such as pullulanase), and glucoamylase.

The invention is accomplished by first extracting the DNA from a bacterial microorganism (the donor microorganism) which is capable of producing at least one amylolytic enzyme, cleaving (with an appropriate restriction enzyme) the DNA plus, as the vector, the DNA of a derivative of phage lambda, and combining the ligating the resulting fragments to form recombinant DNA's, some of which will contain an amylase coding gene. The recombinant DNA's are then made biologically active by inserting into suitable host cells such as *Escherichia coli* (hereafter written *E. coli*) by in vitro encapsidation or transfection.

The resulting clones are then screened for the presence of an amylase coding gene, and one or more positive clones are selected and multiplied, thereby providing new, genetically engineered bacterial microorganisms which are capable of producing, under suitable conditions of cultivation, substantially greater quantities of amylase than can be produced by the donor microorganisms. Optionally, the DNA of the new phage is extracted, cleaved and subcloned into a second vector, which may be either a plasmid or another phage, and the new clones screened and selected on the basis of the presence of an amylase coding gene Successive "sub-subclonings" may also be performed.

In addition to producing new, genetically engineered microorganisms which are "overproducers" of amylase, the invention has the further advantage that it results in the transfer primarily of the gene for the production of a single amylolytic enzyme, thereby minimizing greatly the purification necessary with cultures of nongenetically engineered microorganisms.

Once the genetically engineered microorganism containing the desired recombinant DNA has been produced, the microorganism is cultivated in such a way as to amplify the recombinant DNA and thereby provide amylase in substantially greater amounts than can be provided by the donor microorganism.

When the vector is a derivative of phage lambda, in which case the host microorganism will necessarily be *E. coli*, amplification and enzyme production can be accomplished as follows. If the phage is lytic, the host microorganism, i.e., *E. coli*, is first cultivated to multiply the cells to the appropriate density, they are then infected with a suitable amount of the bacteriophage, and the system is cultivated until the cell walls are destroyed and the amylase escapes into the culture medium.

When the vector-host system is an appropriate lambda lysogenic *E. coli*, the infected host microorganism is first cultivated at 32° C. to multiply the bacterial cells to an appropriate density, after which the temperature is raised to 42° C. and held for a certain time to induce the lytic cycle and then brought to 37° C. and held to cause the amplification of the foreign resident DNA with attendant large amounts of amylase production. The cell walls may be eventually destroyed, depending upon the conditions, in which case the amylase escapes into the culture medium.

When the vector is a multicopy plasmid, such as pBR322 or pACYC184, amplification of the foreign DNA is achieved per se. Alternatively, the genetically engineered microorganism containing plasmid DNA is first cultivated to multiply the bacterial cells to the desired density. Then chloramphenicol is added. Because the antibiotic inhibits protein synthesis, it prevents further cell multiplication and amylase production but permits multiplication (amplification) of the plasmid DNA within the cells. Ultimately, the cells are separated from the culture medium and washed to eliminate the chloramphenicol. For amylase production, the cells are then recultivated, in the absence of chloramphenicol, for the production of massive amounts of amylase.

It is essential in any genetic engineering work, to be able to "mark", and thereby select, those clones containing the desired genetic information. In the practice of the instant invention, this can readily be accomplished by plating on a medium containing starch, if alpha-amylase, beta-amylase or glucoamylase activity is being sought. The culture medium in the plate is then stained with iodine; clones displaying amylase activity on a starch-containing medium are surrounded by a white area. A specific, preferred staining method will be described hereinafter. If pullulanase activity is being sought, the clones are plated on a BBL Trypticase medium containing pullulan. This technique is described in more detail hereinafter.

Donor Microorganism: The donor microorganism should be a bacterial microorganism capable of producing at least one amylase (including, of course, the desired amylase), and advantageously will produce an amylase having properties which are desirable in the industrial hydrolysis of starch, e.g., resistance to high temperature or metal poisoning. Because of the relative simplicity in working with a prokaryotic source of DNA as compared to the eukaryotes, our work has been confined to bacteria, and our invention is, therefore, limited to the use of a bacterial donor. As will be seen from the examples, we have successfully employed strains of *B. megaterium, B. coagulans, B. cereus* and *K. pneumoniae* to produce genetically engineered microorganisms capable of producing massive amounts of alpha-amylase, heat-resistant alpha-amylase, beta-amylase and pullulanase, respectively.

Ligating and Restriction Enzymes: In our work, we have consistently used as ligating enzyme, T4 DNA ligase, but it will be readily understood that any DNA-ligating enzyme can be employed. The specific restriction enzymes employed in our work are set forth in the examples. The selection of a suitable restriction enzyme can, of course, be made by the skilled practitioner employing well-known techniques. Our method for selecting a restriction enzyme for further experimentation has been to cleave the DNA extracted from the donor microorganism (the donor DNA) by different restriction enzymes and select the one (or more than one) most suitable for further experimentation based on the ability of the enzyme to cut the DNA in numerous fragments of sizes ranging between 2 and 15 kilobases (Kb).

There are several reasons why derivatives of phage lambda are particularly efficacious for the cloning of the DNA extracted from the donor: (1) Deletion mutants of phage lambda permit insertion of foreign DNA fragments of various sizes (depending, of course, on the specific lambda derivative), and furthermore permit simple identification of those clones which contain foreign DNA. (2) Different derivatives of phage lambda have been developed which allow the use of several restriction enzymes, thus increasing the chances of realizing a successful cloning. (3) Very good amplifications of foreign genes are possible using appropriate derivatives of phage lambda. (4) After ligation, the recovery of recombinant clones is done easily by transfection or in vitro packaging. Because of its versatility, which no other presently existing vector can provide, we employ, in the practice of the invention, derivatives of phage lambda, and *E. coli* as the host, for the initial cloning of the DNA extracted from the donor.

Other advantages to using a phage, rather than a plasmid, for the primary cloning are the following: (1) the percentage of clones having foreign DNA inserts is higher; (2) the bacteria are lysed, thus liberating the cell contents, and therefore any amylase, into the medium, thus facilitating the detection by the iodine staining technique; (3) the resistance of phage lambda toward iodine is higher than that of *E. coli.*

The selection of a suitable plasmid as a vector for a subcloning is well within the skill of the competent geneticist, one criterion being, of course, the existence of a single or a limited number of restriction sites for the restriction enzyme to be employed.

The plasmids employed in most of our work are pBR322 and pACYC184. In its intact state, plasmid pBR322 confers resistance to both ampicillin and tetracycline, and contains a single restriction site for each of Pst I, Eco RI, Hind III, Bam HI and Sal I enzymes. Cutting and insertion at the Pst I site destroys the capacity to confer resistance to ampicillin, while insertion into the Bam HI and the Sal I sites will destroy the resistance to tetracycline. Insertion into the Hind III site sometimes destroys the resistance to tetracycline, provided that the cloned gene does not possess its own promoter.

In its intact state, plasmid pACYC184 confers resistance to both tetracycline and chloramphenicol, and contains single restriction sites for each of Eco RI, Hind III, Bam HI and Sal I enzymes. Cutting and insertion at the Eco RI site destroys the capacity to confer resistance to chloramphenicol, while insertion into the three other sites for Hind III, Bam HI and Sal I have the same effects as in plasmid pBR322, since this region is common to both plasmids.

For subcloning into *B. subtilis*, we used plasmid pC194 as a vector. This plasmid has a single Hind III site and confers resistance to chloramphenicol.

Host Microorganism: Because derivatives of phage lambda can be expressed only in *E. coli*, this must, obviously, be the host for recombinant phage DNA prepared in accordance with the invention. When the recombinant DNA is in the form of a plasmid, on the other hand, any microorganism which is capable of accepting and replicating such plasmid DNA, e.g., other bacterial microorganisms, or yeasts such as *Saccharomyces cerivisiae*, can be employed.

For practical reasons, we have used *E. coli* strains (e.g., HB101) in most of our work because they are well-known strains from the genetic point of view and are susceptible to infection by known phages and plasmids with consecutive enhanced capacity of enzyme overproduction.

As is described in Example IIA, a recombinant plasmid can be subcloned into a plasmid such as pC194, capable of replicating in *B. subtilis*.

Process: The process will be described in terms of a two-stage cloning experiment, the first stage (shotgun) employing a phage and the second employing a plasmid.

Having selected the donor microorganism, the restriction and ligating enzymes and the specific derivative of phage lambda, the DNA's are extracted, restricted, mixed, and the joined pieces are ligated, all by conventional techniques which need no description here.

The DNA is then made biologically active in an *E. coli* by transfection or in vitro encapsidation. In our work with lambda DNA, we have had very good success using the technique of encapsidation. (B. Hohn and K. Murray, Proc. Natl. Acad. Sci. USA, 74, 3259-3263, 1977.) Those clones which have received foreign DNA are then identified by appropriate methods. If an insertion vector such as lambda NM590 or lambda NM607 is employed, those clones containing foreign DNA give clear plaques, while those not containing foreign DNA give turbid plaques. When a replacement vector such as lambda NM761 or lambda NM781 is used, the identification can be made by plating on an *E. coli* lac amber recipient on lactose indicator medium, e.g., McConkey, EMB or x gal.

Many (several thousand) of the clones which have accepted foreign DNA are then plated onto media containing starch and screened for the presence of an amylase-coding gene by the iodine staining method mentioned previously. Care must be taken, of course, not to employ so high a concentration of iodine to kill the phage, and this can be a problem if the iodine is added in the form of a solution. Our greatly preferred staining technique is to expose the plates to iodine vapors for a short time; we have employed this technique with very good success.

A preferred method for detecting clones having pullulanase activity, which method does not employ iodine staining, will now be described. The phages are plated on petri dishes containing BBL Trypticase plus pullulan at a concentration of about 0.25%. The pullulan in the medium around the "positive" plaques is hydrolyzed to maltotriose by the pullulanase, which maltotriose is used by the bacteria. Therefore, those bacteria feeding on the maltotriose grow better than the others in the lawn, with the consequence that the plaques producing pullulanase are surrounded by an opaque ring of growing bacteria and can be detected readily. This technique is described in detail in Example IV.

One (or more) positive clone is then picked and multiplied. This can, of course, comprise the "final" genetically engineered microorganism, and it can be used to produce large amounts of amylase by appropriate cultivation as described previously. Alternatively, the clone can be used as a source of DNA for a second cloning into a plasmid or another, more suitable phage. The process of subcloning into a plasmid will now be described.

Again, using standard techniques, the DNA of the clones is extracted and cleaved with a restriction enzyme; the plasmid is similarly cleaved; the fragments are mixed and the recombined fragments are ligated. When using plasmid pBR322, identification of clones which have accepted DNA containing an amylase coding gene is accomplished by making the DNA biologically active in a host such as *E. coli* by transformation, in a culture medium containing ampicillin or tetracycline, depending upon the restriction enzyme used. The culture medium will also contain starch or pullulan and identification of clones containing the amylase coding gene is made by one of the techniques described previously. Positive clones are then cultivated and the plasmid DNA can then be amplified by means of chloramphenicol, as described previously.

The examples will exemplify the practice of the invention. They are presented for illustrative purposes only, and should not be construed as limiting the invention in any way. Percentages are by weight unless specified otherwise.

EXAMPLE I

Cloning of an alpha-Amylase Gene

The following materials were used:

Restriction endonuclease Hind III*
T4 DNA ligase*
Phage lambda NM590
  (The phage DNA was prepared by phenol extraction from highly purified phage particles.)
*These enzymes and other endonucleases were obtained from Boehringer Mannheim, GmbH, Mannheim, West Germany.
Plasmid pBR322
  (Plasmid DNA was purified from lysozyme-lysed *E. coli* cells in cesium chloride-ethidium bromide density gradients.)
Host microorganism, *E. coli* HB101

The donor microorganism was a strain of *B. megaterium* having the following microbiological characteristics:

| | | |
|---|---|---|
| (1) | Morphology: | Rods (0.5 to 0.7μ × 2.0 to 5.0μ), motile, gram positive, spores are terminal to subterminal. |
| (2) | Nutrient Broth: | Good growth |
| (3) | Nutrient Agar Broth: | Good growth; the colonies are dense in the middle and more diffuse around. |
| (4) | Milk: | Peptonization without change of pH value. |
| (5) | Gelatin: | Not liquefied. |
| (6) | Reduction of Nitrates: | Negative |
| (7) | Catalase Reaction: | Negative. |
| (8) | Oxidase Reaction: | Negative. |
| (9) | Cytochrome Oxidase Reaction: | Negative. |
| (10) | Production of Indole: | Negative. |
| (11) | Formation of H$_2$S: | Negative. |
| (12) | Utilization of Carbohydrates: | Utilizes arabinose, xylose, galactose, glucose, levulose, maltose, raffinose, saccharose, starch and produced acid from them. Rhamnose, mannose, melibiose, inuline and salicine are not utilized. |
| (13) | Polyols Utilization: | Sorbitol and mannitol are utilized; adenitol, dulcitol and inositol: no. |
| (14) | Decarboxylase Reaction on Lysine: | Negative. |
| (15) | Ureolyse: | Weak. |
| (16) | Resistance to Heavy Metals: | Grows directly on 500 ppm Cr$^{+++}$. |
| (17) | Sodium Chloride Broth: | Growth at NaCl concentration of 3.5%. |
| (18) | Temperature for Growth: | Optimum - 30-37° C. Maximum - 40-50° C. Minimum - 5-20° C. |
| (19) | Oxygen Requirement: | Aerobic. |

The microorganism was identified as *B. megaterium* on the basis of its microbiological characteristics with reference to Bergey's Manual of Determinative Bacteriology (Eight Edition), R. E. Buchanan and N. E. Gibbons, co-editors; published by The Williams and Wilkins Company, Baltimore, Md. The microorganism has been deposited with the National Collection of Industrial Bacteria (NCIB), Torry Research Station, P.O. Box No. 31, 135 Abbey Road, Aberdeen AB9 8DG, Scotland on Feb. 12, 1980, and has been given NCIB No. 11568.

Following is a description of the process used:

A. In Vitro Recombination Between Lambda and *B. megaterium* DNA's

About 7 μg of *B. megaterium* DNA was cleaved with 10 units of Hind III at 37° C. for 1 hour in a volume of 25 μl of tris(hydroxymethyl)aminomethane hydrochloride (hereafter written Tris-HCl) buffer at pH 7.5. About 2 μg of lambda NM590 was similarly cleaved with the same enzyme. The reactions were stopped by heating at 75° C. for 10 minutes.

Two tests were performed to determine the efficiency of the cleavage:
  1. A sample of the two reaction mixtures was electrophoresed in an agarose gel for 20 hours at 20 volts. After staining the gel with ethidium bromide, the expected pattern of bands was observed: 2 bands of lambda DNA resulting from the cleavage of the single Hind III site on lambda DNA, and a very large number of almost overlapping bands from the bacterial DNA cleaved at a large number of sites.
  2. Transfection assay of the phage DNA showed that the cleavage had been more than 99% efficient, thus destroying almost completely the biological activity of the phage DNA.

The cleaved DNA's were mixed and incubated for 5 hours at 10° C. with 0.15 units of T4 DNA ligase, to allow random reannealing and covalent sealing of the DNA fragments.

At the end of this incubation, the DNA was mixed with an in vitro encapsidation preparation consisting of a mixture of two complementary defective phage lysates (lambda Dam and lambda Eam) induced from nonsuppressive strains. In this mixture, any DNA molecule having the cos extremities of lambda DNA and being of the appropriate size can be incorporated into phage protein, thus reconstituting in vitro a biologically active phage particle able to infect *E. coli* and to produce an infection center (plaque).

To assess the efficiency of this process, two controls were performed:
  1. A sample of the mixture was plated on *E. coli*, 3×10$^5$ plaques were found per μg of the input lambda DNA. This was about 100-fold more than found in the cleaved preparation, indicating a good efficiency of the ligase treatment.
  2. The plaques thus formed were examined visually. 70% of them were clear instead of turbid, indicating the presence of a fragment of *B. megaterium* DNA, splicing and therefore inactivating the lambda gene Cl, responsible for plaque turbidity.

Thus, one could assess that the preparation contained a random sample of all *B. megaterium* possible Hind III DNA fragments compatible with insertion into phage lambda NM590.

B. Isolation of a Phage Lambda Derivative Carrying *B. megaterium* Amylase

The remainder of the encapsidation mixture was used to inoculate *E. coli* on large number of starch-containing plates with about 10$^3$ viable particles per plate. After growth of the infected *E. coli* and formation of the plaques, the plates were screened for the presence of starch-degrading plaques. This was done by exposing the plates to iodine vapors for a short time; it was expected that the plaque formed by such a phage would be surrounded by a clear area, resulting from the diffusion and action of amylase from the lysed cells. One such plaque was found and the phage it contained was immediately picked for subculturing (a longer exposure to iodine vapors would have killed the phage). The progency of this plaque bred true (amylase producing) and is designed by us as "lambda NM590 Amy 1". Phage lambda NM590 Amy 1 was deposited with the NCIB on Feb. 12, 1980, as NCIB No. 11569.

C. Recloning the Amylase Gene into Plasmid pBR322

The amylase gene was recloned into plasmid pBR322 both to obtain an overproducing strain and to prepare easily a large amount of DNA with the amylase gene.

1 µg of DNA from the lambda NM590 Amy 1 and 0.3 µg of plasmid pBR322 DNA were cleaved, mixed and treated with ligase, as described in Section A. This preparation was used to transform (using usual methods) the strain HB101. Selection was for ampicillin (Ap) resistance, a property conferred to the cells by the presence of this plasmid. This plasmid confers normally also resistance to tetracycline (Tc). However, the introduction of foreign DNA in this plasmid splits the TC gene, thus, the proportion of tetracycline-sensitive transformed clones reflects the proportion of plasmids containing cloned DNA. In this case, 16% of the clones contained a new plasmid which conferred amylase activity (Amy+) to $E.$ $coli.$ (According to the current international nomenclature of plasmids, the new plasmids to be described here are named (pCP), and the specific plasmid of this example is designated as (pCP 1).

This demonstrates that recloning a gene with the same enzyme (in this case Hind III) is a very efficient process (16% instead of $1/10^5$).

Figure 1:
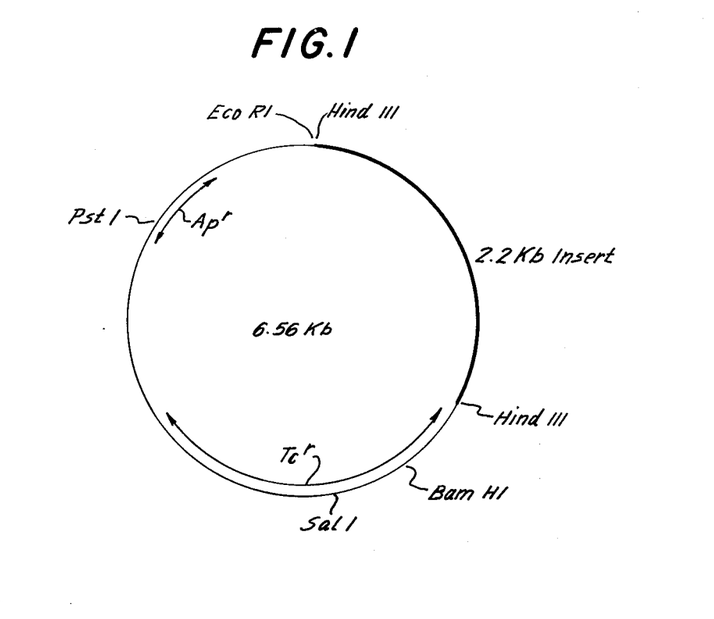
FIG. 1 is a map of the plasmid pCP 1 obtained by inserting a DNA fragment containing an alpha-amylase coding gene from *B. megaterium* (*Bacillus megaterium*) into pBR322.

The plasmid-containing microorganism is designated as $E.$ $coli$ CL7001 (pCP 1) and was deposited with the NCIB on Feb. 12, 1980, as NCIB No. 11570. The map of pCP 1 is shown in FIG. 1.

D. Amplification and Enzyme Production

Enzyme production in plasmid (pCP 1)-containing cells was improved in two ways, as follows:
1. Saturated Cultures Cultures were incubated overnight at 37° C. on a rotary shaker in 5-liter baffled Erlenmeyer flasks containing 1 liter of culture medium (LB: yeast extract-tryptone).
2. Chloramphenicol Amplification Cultures were incubated at 37° C. on a rotary shaker in 5-liter baffled Erlenmeyer flasks containing 1 liter of culture medium (LB) until a density of 0.8 (650 nm) was reached, at which point 150 µg/ml of chloramphenicol was added. This prevented further replication of the chromosomal DNA but not that of the amylase gene-containing plasmid (pCP 1). After amplification (up to 3,000 copies) of the plasmid, compared to chromosomal DNA, chloramphenicol was removed to allow protein synthesis to resume. Specifically, after amplification the cells were separated from the medium by centrifugation, washed to eliminate chloramphenicol, and recultivated for amylase production.

E. Enzyme Recovery

We employed the "osmotic shock" method to recover the alpha-amylase in very pure form. The process, which is reported by H. C. Neu and L. A. Heppel in $J.$ $Biol.$ $Chem.,$ 240, 3685-3692 (1965), was as follows.

The cells were first cultured overnight, after which they were suspended in a 25% sucrose solution in 0.5 volume of culture and shaken for 10 minutes at 24° C., which treatment plasmolyzes the cells. Ethylenediaminetetraacetic acid (hereafter written EDTA) was then added to a final concentration of 1 mM to render the cell walls permeable, and the material was shaken for another 10 minutes at 24° C. The suspension was centrifuged and the cells were quickly resuspended in cold (about 0° C.) water and shaken at this temperature for 10 minutes. The suspension was again centrifuged and 96% of the enzyme was recovered from the supernatant.

For comparison, the donor microorganism ($B.$ $megaterium$) was cultivated and the enzymatic activity determined. The amount of enzyme per ml of culture medium was measured by the DNS (dinitrosalicylic acid) method described in Anal. Biochem., 45, 510 (1972), one enzymatic unit being defined as the amount of enzyme producing 1 mg of reducing sugar (using maltose as reference) per minute for a 10-minute incubation time. The substrate was very pure amylose.

The donor microorganism produced 66.0 enzymatic units/liter of culture. $E.$ $coli$ CL7001 (pCP 1) saturated cultures produced 116.6 units/liter of culture, while after cultivation (amplification) for 5 hours with chloramphenicol followed by 15 hours without chloramphenicol $E.$ $coli$ CL7001 (pCP 1) produced 84.5 units/liter. This demonstrates that the saturated culture method is sufficient to provide good enhancement of enzyme production.

The enzyme produced by $E.$ $coli$ CL7001 (pCP 1), which is identified as an alpha-amylase, has the following characteristics. It cleaves both amylose and amylopectin into glucose, maltose and maltotriose, principally maltose, and it cleaves both cyclodextrin and maltotriose into glucose and maltose. It cleaves pullulan into panose and/or iso-panose, which is a property similar to that of an enzyme recently described by Shimizu, et al, "Purification and Some Properties of a Novel Alpha-Amylase Produced by a Strain of $Thermoactinomyces$ $vulgaris$", Agric. Biol. Chem., 42 (9), 1978, pp. 1681-1688.

The microorganism herein called $B.$ $megaterium$ was once thought by us to be $Bacillus$ $circulans.$

EXAMPLE II

Cloning of a Thermostable alpha-Amylase Gene

The donor microorganism was an original strain of Bacillus isolated from a compost and identified as a $B.$ $coagulans.$ It produces a thermostable alpha-amylase, and has the following microbiological characteristics:

| | |
|---|---|
| (1) Morphology: | Rods (0.6 to 1µ × 2.5 to 5.0µ), motile gram positive and negative. Spores are central or terminal, not deforming. |
| (2) Nutrient Broth: | Good growth. |
| (3) Nutrient Agar Slant: | Good growth, filamentous, spreading, creamy white. |
| (4) Organic Acid Utilization: | Citrate: positive Malonate: negative |
| (5) Gelatin: | Liquefaction. |
| (6) Production of Acetylmethyl Carbinole | Positive. |

-continued

| (Acetain): | |
|---|---|
| (7) Orthonitrophenyl Galactoside Hydrolysis: | Positive. |
| (8) Reduction of Nitrates: | Positive, gas may be produced. |
| (9) Catalase Reaction: | Positive. |
| (10) Production of Indole: | Negative. |
| (11) Decarboxylase Reaction on: | Lysine: negative Ornithine: negative Arginine: negative |
| (12) Formation of $H_2S$: | Negative. |
| (13) Utilization of Carbohydrates: | Utilizes arabinose, galactose, glucose, levulose, mannose, maltose, saccharose, starch, trehalose and produced acid from them. |
| (14) Pullulan is utilized on minimum medium. | |
| (15) Utilization of Polyols: | Glycerol, sorbitol, mannitol, inositol are utilized. Adonitol, dulcitol: no. |
| (16) Ureolyse: | Negative. |
| (17) Lecithin Utilization: | Negative. |
| (18) Temperature for Growth: | Optimum - 50° C. Maximum - 55–60° C. Minimum - 15–25° C. |
| (19) Oxygen Requirement: | Aerobic and anaerobic. |

The strain was deposited with the NCIB on Feb. 12, 1980, as NCIB No. 11571.

The DNA was extracted and submitted to the action of Eco RI; Hind III; Pst I; Sal I; Bam HI and Bgl II. Only Bgl II was able to generate many fragments of a wide range of molecular weights. It was, however, possible to generate fragments with Eco RI, when the NaCl concentration was decreased to 50 mM. We therefore decided to use Eco RI to generate fragments for cloning into an Eco RI lambda DNA vector (lambda NM781).

A. Restriction of *B. coagulans* and Lambda NM781 DNA's 1.25 μg of lambda NM781 DNA was cut by one unit of Eco RI in 25 μλ of the following buffer:
10 mM Tris-HCl (pH 7.5)
10 mM 2-mercaptoethanol
10 mM $MgSO_4$
100 mM NaCl 2 μg of *B. coagulans* DNA was cut by the same enzyme in a similar buffer, except that the NaCl concentration was lowered to 50 mM. The incubation was done for 2 hours at 37° C. and the reaction was stopped by heating for 10 minutes at 75° C. The completeness of the restriction was controlled by electrophoresis in 1% agarose gels.

B. Ligation and Recovery of Recombinant Phages

The restricted DNA's were mixed and ligated using 2 units of T4 DNA ligase in a mixture containing 60 mM Tris-HCl (pH 8), 10 mM $MgSO_4$, 10 mM 2-mercaptoethanol and 0.1 mM adenosine triphosphate (hereafter written ATP). The reaction was done for 10 to 15 hours at 10° C. After the ligation, aliquots of 0.2 μg of DNA were mixed with ATP to give a final concentration of $10^{-2}$M. These aliquots were submitted to in vitro encapsidation and used to infect strain HB101 of *E. coli*.

About $1.6 \times 10^4$ PFU (Plaque Forming Units) were obtained per μg of lambda DNA. Among these phages, some showed an amylase activity (for the detection of amylase activity on petri plates and for the recovery and purification of the phage, see Example I).

A rather high proportion of amylase-producing phages was observed (1 in 400).

One was selected and is designated as "lambda NM718 alpha Amy 1". It was deposited with the NCIB on Feb. 12, 1980, as NCIB No. 11572.

C. Recloning of the Amylase Gene from Lambda NM781 Alpha Amy 1 into Plasmid pBR322

Figure 2:
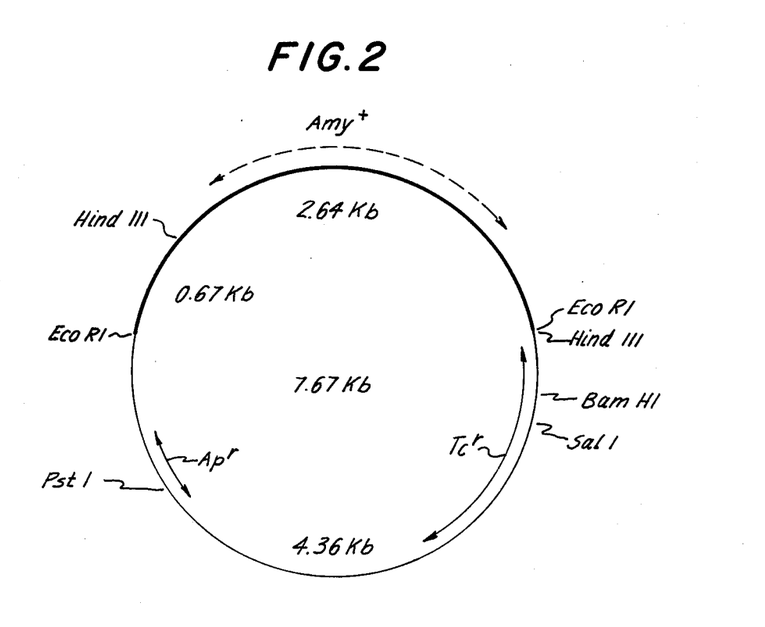
FIG. 2 is a map of the plasmid pCP 2 obtained by inserting a DNA fragment containing a thermostable alpha-amylase coding gene from *B. coagulans* (*Bacillus coagulans*) into pBR322.

1 μg of lambda NM781 alpha Amy 1 DNA and the same amount of DNA from the plasmid pBR322 were cut with Eco RI, using the usual conditions. The ligation and transformation were done as explained in Example I. Colonies of *E. coli* HB101 containing recombinant plasmid were detected by their amylase activity. One such colony was selected, and is designated *E. coli* CL7002 (pCP 2). It has been deposited with the NCIB on Feb. 12, 1980, as NCIB No. 11573. The map of pCP 2 is shown in FIG. 2.

D. Amplification of the Gene Product

Amplification of the amylase coding gene of lambda NM781 alpha Amy 1, and amylase production, were accomplished as follows. The host bacteria (*E. coli* HB101) were grown in LB medium with 2 mM $MgCl_2$ at 37° C. until an optical density of 0.3 (at 650 nm) was reached. The lambda NM781 alpha Amy 1 was then added, the number of phages being calculated to get a multiplicity of infection of about 1–2, i.e., one or two phages per bacterial cell. The culture was then continued with vigorous agitation at 37° C. and the optical density was followed until it started to drop. When it had dropped to below 0.5, the culture was harvested and put on ice. The culture was centrifuged and the supernatant was tested for amylase activity.

Amplification and enzyme production with *E. coli* CL7002 (pCP 2) were accomplished using both the saturated culture method and chloramphenicol amplification as in Example I.

The amylase activity was determined using the DNS method both in the phage lysate and in cultures of *E. coli* harboring the recombinant plasmid. Table I shows the values obtained for the amylase activity in the original strain of *B. coagulans* and the repartition between the extracellular and cell-bound activity. The activities obtained with the recombinant phage (lambda NM781 alpha Amy 1) and the strain harboring the recombinant plasmid *E. coli* CL7002 (pCP 2) are also given. An enhancement of enzyme production of about 3 times was obtained with the recombinant phage, and an even much better enhancement was observed with the plasmid (about 300 times).

In the case of the phage (lambda NM781 alpha Amy 1), all of the enzyme is liberated upon cell lysis and consequently is present in the culture medium. In the case of the plasmid, most of the enzyme is cell-bound (96%).

E. Recloning into a Derivative of Phage Lambda Capable of Lysogenizing *E. coli*

To illustrate the preparation of a vector-host system comprising a lambda lysogenic *E. coli*, the following experiment was performed.

Bacteriophage lambda T4 lig. CI857 Wam Eam Sam (lambda NM989) was employed. It is described in J. Mol. Biol., Vol. 132 (1979). "Molecular Cloning of the DNA Ligase Gene from Bacteriophage T4. I., Characterization of the Recombinants" by G. G. Wilson and Noreen E. Murray (pp. 471-491) and "II., Amplification and Separation of the Gene Product" by Noreen E. Murray, S. A. Bruce and K. Murray (pp. 493-505).

This phage contains the DNA ligase gene of bacteriophage T4 and is able to lysogenize E. coli. It has, moreover, a thermosensitive immunity gene and two amber mutations in the E gene and the S gene, respectively. The mutation of the S gene makes the bacteria no longer lyse upon infection with this phage. The purpose of the subcloning was to replace the DNA ligase gene with the amylase coding gene.

The DNA of the phage and plasmid (pCP 2) were cut with Eco RI and the fragments ligated. The phage DNA resulting from the ligation was then in vitro packaged and the plaques visualized by plating on a strain of E. coli Sup E Sup F. The plaques showing amylase activity were picked and the phage was purified using the techniques described previously.

This phage was then used to lysogenize a strain of E. coli C600 (CL1205) using conventional techniques. The lysogenic colonies were visualized on a starch-containing medium using iodine staining. This strain has been designated by us as E. coli CL7003 (lambda alpha Amy 1), and was deposited with the NCIB on Mar. 6, 1980, as NCIB No. 11586.

Amplification of the gene product was accomplished in the following way. The lysogen was grown at 32° C. in LB medium until a density of 0.8 at 650 nm was reached, then centrifuged and the cells were suspended in fresh LB medium which had been prewarmed at 45° C. The culture was then incubated in a 45° C. bath for 15 minutes in order to induce the lytic cycle (since the immunity gene product is thermosensitive).

The incubation was then continued with vigorous shaking at 37° C. for 3 hours. The amylase activity was then measured in the supernatant and in the cells. The values are reported in Table I.

Eam Sam. Alternatively, the donor DNA could have been cloned directly into the latter-mentioned phage, any number of variations of the exemplified process being feasible.

F. Recovery and Characterization of the Amylase Produced by Lambda NM781 Alpha Amy 1, E. coli CL7002 (pCP 2) and E. coli CL7003 (Lambda Alpha Amy 1)

As in Example I, we employed the osmotic shock method for recovery of the enzyme. In addition, because the enzyme of this example is thermostable, it could be further purified by adding to the aqueous solution 10 mM $Ca^{++}$ and warming the solution to 80° C. and holding for 10 minutes. This treatment precipitates all of the E. coli proteins and permits recovery of the alpha-amylase in extremely pure form, virtually no debris or other enzymes being present.

The specificity of the alpha-amylase was determined: it is active on amylose and starch, the products of hydrolysis are glucose, maltose and maltotriose with traces of higher molecular weight components. This enzyme is not active on cyclodextrin. The thermostability of the enzyme was also studied, and was shown to be very high. The optimum temperature for activity with 0.5% amylose is between 80° C. and 90° C. With 8% soluble starch, the optimum is situated around 100° C.

It is possible that the microorganism herein called B. coagulans is in fact Bacillus licheniformis.

EXAMPLE IIA

Subcloning of Plasmid pCP 2 into Plasmid pC194 and Expression of the New Plasmid in Bacillus subtillis This example illustrates a technique whereby recombinant DNA prepared in accordance with the invention can be expressed in a host bacterium other than E. coli, namely, a strain of B. subtilis.

Plasmid pCP 2, from Example II, contains a 3.31 Kb fragment from the B. coagulans donor; the plasmid is further characterized by conferring ampicillin and tetracycline resistance, and it contains two restriction sites for each of Eco RI and Hind III. Plasmid pCP 2 was

TABLE I

AMYLASE ACTIVITY, IN UNITS[a]/LITER, IN THE ORIGINAL STRAIN OF B. coagulans AND IN THE RECOMBINANT CLONES OF EXAMPLE II

| | Supernatant | Periplasmic | Cells | Total | Enhancement of Enzyme Production |
|---|---|---|---|---|---|
| B. coagulans | 42 | — | — | 42 | 1 |
| Lambda NM781 Alpha Amy 1 | 144 | — | — | 144 | 3.43[a] |
| E. coli CL7002 (pCP 2) with Cm amplification | 230 | — | 5,700[b] | 5,930 | 141.2[a] |
| E. coli CL7002 (pCP 2), overnight cultures | 276.2 | 12,960 | 232 | 13,467 | 320.6[a] |
| E. coli CL7003 (lambda alpha Amy 1) | 23 | — | 1,162[b] | 1,185 | 26.1[a] |

[a]1 unit (U) is defined as the amount of enzyme that give 1 mg of maltose equivalent per ml per minute at 50° C. using 0.5% amylose as substrate.
[b]The osmotic shock method was not used, but a lysis was done, so this value represents the sum of the amylase activity in the periplasm and the cells.

This particular experiment illustrates a "sub-subcloning" technique from the plasmid into a new lambda phage. It will be readily understood that the DNA from lambda NM781 alpha Amy 1 could just as easily have been subcloned into phage lambda T4 lig. CI857 Wam cleaved into 4 fragments by using both Eco RI and Hind III. The resulting fragments were treated with ligase, and used to transform HB101 as in the previous examples.

Figures 3A, 3C:
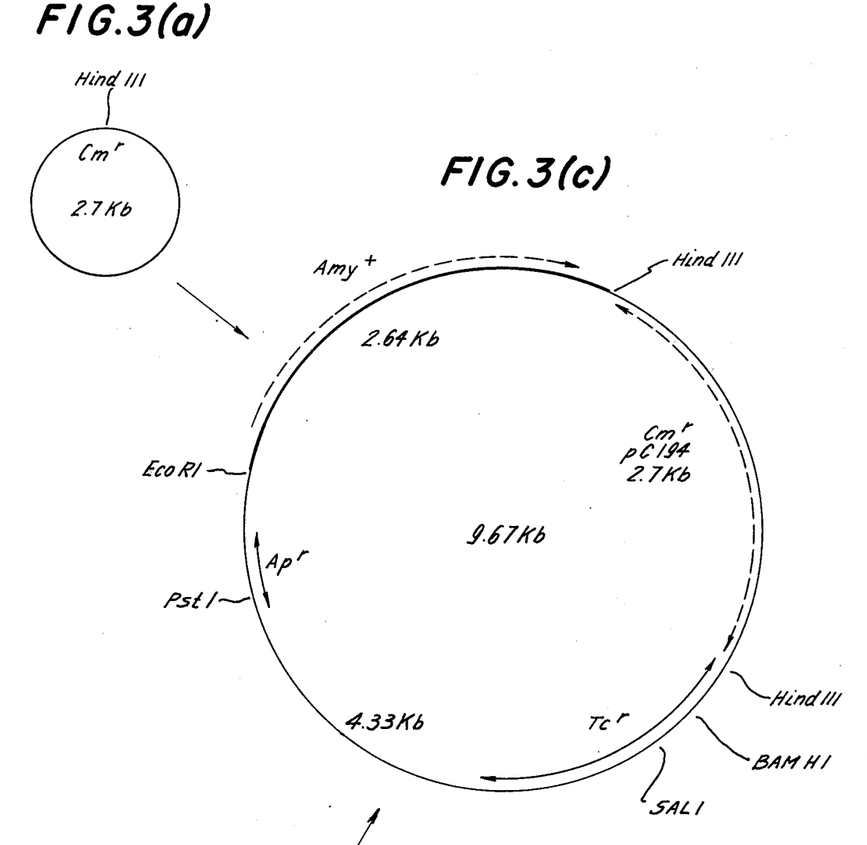
Figure 3B:
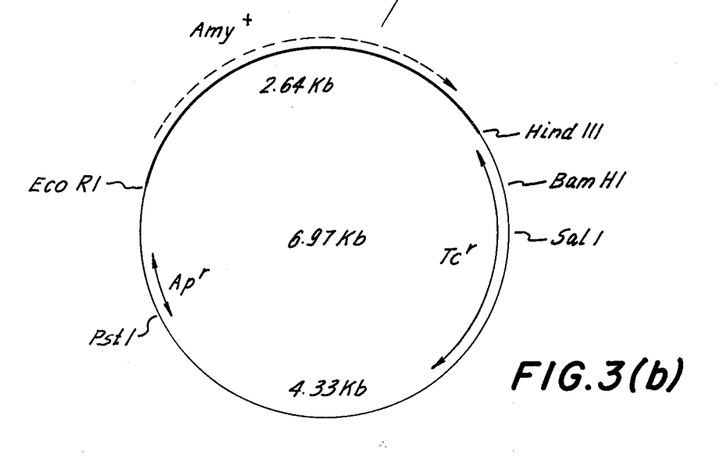

A new plasmid, designated by us as pCP 2.3, was formed, having a 2.64 Kb fragment of the *B. coagulans* DNA, said fragment containing the alpha-amylase coding gene. As shown in FIG. 3(b), pCP 2.3 has a single site for each of Eco RI and Hind III, and confers both ampicillin and tetracycline resistance.

For the next step, plasmid pC194 was selected as a vector. This plasmid is known to be capable of replicating in *B. subtilis*. pC194 confers chloramphenicol resistance, and has a single Hind III site. Both pCP 2.3 and pC194 were opened with Hind III, mixed and ligated to form a new plasmid, designated as pCH 1. As shown in FIG. 3(c), this plasmid contains the alpha-amylase coding gene and possesses chloramphenicol resistance and ampicillin resistance, although the level of chloramphenicol resistance was low in *E. coli*. As before, the preparation was used to transform *E. coli* HB101.

The mutant strain of *B. subtilis* designated as QB1133 (received from Dr. Michel Steinmetz, Institut de Recherche en Biologie Moléculaire, Université Paris VII, Tour 43, 2 Place Jussieu, 75221 Paris Cedex 05) has no alpha-amylase activity. It was treated in accordance with the technique of S. Chang and S. Cohen, Molec. Gen. Genet., 168, 111–115 (1979), to form protoplasts. The protoplasts were then transformed with pCH 1 using the polyethylene glycol mediated transformation procedure of Chang and Cohen (ibid.).

The protoplasts were then incubated in a rich medium for 1.5 hours in order to permit the plasmid in the bacteria to express the resistance to chloramphenicol.

The protoplasts were then plated on a regeneration medium to which had been added chloramphenicol in an amount of 20 μg/ml. After 2 days of incubation at 37° C., colonies of transformed cells had appeared; those colonies having alpha-amylase activity were detected by the iodine vapor staining technique. One clone, designated as *B. subtilis* CL8001 (pCH 1), was deposited on Jan. 13, 1981, as NCIB No. 11629. The original strain QB1133 was also deposited on Jan. 13, 1981, as NCIB No. 11628.

*B. subtilis* CL8001 (pCH 1) is stable only in the presence of chloramphenicol. It can be used to produce alpha-amylase by cultivating in a medium containing chloramphenicol (20 μg/ml). The alpha-amylase can readily be recovered in the culture fluid.

After an overnight culture in the presence of chloramphenicol, the quantity of alpha-amylase produced was determined as follows:

| Supernatant | Cells | Total |
|---|---|---|
| U/l | U/l | U/l |
| 136 | 14 | 150 |

EXAMPLE III

Cloning of a beta-Amylase

The donor microorganism was a strain of *B. cereus* which is described in British Pat. No. 1,466,009 of the Agency of Industrial Science & Technology (Japan). It was deposited with the Fermentation Research Institute of Chiba-shi, Japan on Dec. 20, 1973, as FERM-P No. 2391 and also was deposited with the American Type Culture Collection as ATCC No. 31102 on Dec. 26, 1974. It is known to produce both beta-amylase and alpha-1,6-glucosidase.

A. Cloning of the beta-Amylase Gene in Lambda NM781

The methods used for the restriction, ligation and recovery of the recombinant phages were the same as for Example II. The DNA (2 μg) of *B. cereus* was restricted under the normal conditions by the Eco RI restriction enzyme. The phage vector DNA (1.25 μg of lambda NM781) was also cut by Eco RI. The ligation and packaging were performed as described previously.

Several recombinant phages displaying amylase activity were discovered (about 1 to 500). One of these phages (designated as "lambda NM781 beta Amy 1) was selected; it was deposited with the NCIB on Feb. 12, 1980, as NCIB No. 11574.

B. Recloning of the beta-Amylase Gene from Lambda NM781 Beta Amy 1 into Plasmid pBR322

In order to increase the production of enzyme, this first beta-amylase clone was used as a source of beta-amylase coding DNA to subclone it into the multicopy plasmid pBR322.

2 μg of lambda NM781 beta Amy 1 DNA and 1 μg of pBR322 were cut with Eco RI, mixed and treated with $T_4$-ligase. Ligation and transformation were realized as described previously.

Figure 4:
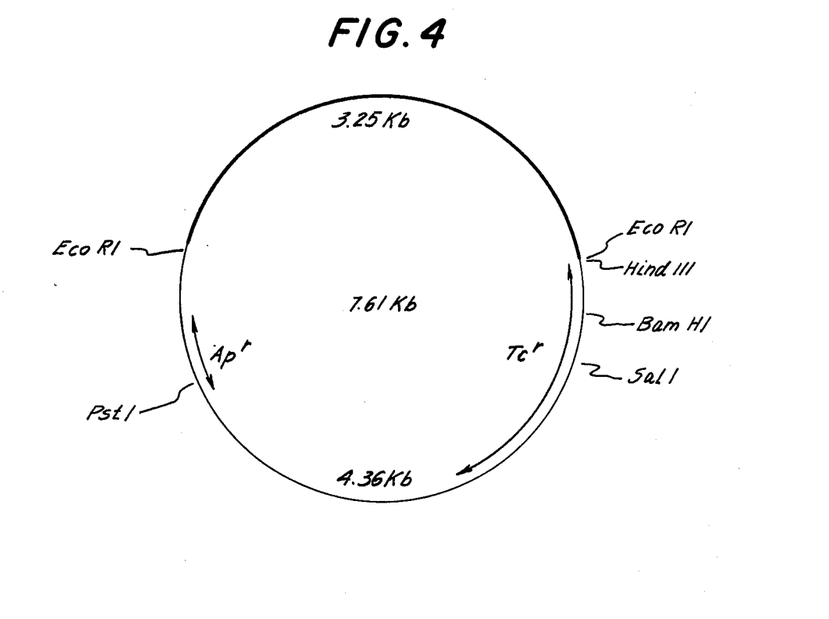
FIG. 4 is a map of the plasmid pCP 3 obtained by inserting a DNA fragment containing a beta-amylase coding gene from *B. cereus* (*Bacillus cereus*) into pBR322.

One colony on 200 ampicillin resistant colonies showed a starch degradating activity. One was isolated and designated *E. coli* CL7004 (pCP 3); it was deposited on Sept. 15, 1980, as NCIB No. 11602. The map of pCP 3 is shown in FIG. 4.

C. Recloning of the beta-Amylase Gene into a Derivative of Phage Lambda Capable of Lysogenizing *E. coli*

The vector employed was the thermosensitive lambda $T_4$ lig. phage CI857 Wam Eam Sam (lambda NM989) described in Example II. About 1 μg of the plasmid pCP 3 DNA and 0.5 μg of the phage DNA were cleaved, then the fragments ligated together and the resulting pieces of DNA packaged in vitro. The phage particles displaying an amylase activity were isolated and utilized to obtain lysogenic colonies by the same method as before. The strain *E. coli* C600 lysogenic for this recombinant phage was isolated and designated as *E. coli* CL7005 (lambda beta Amy 1); this was deposited on Sept. 15, 1980, as NCIB No. 11603.

D. Amplification of the Amylase Gene Product

In all clones and subclones, the amylase activity was detected by the DNS method. The beta-amylase activity was confirmed on thin layer chromatograms by the presence of a single spot of maltose after digestion of amylose.

Amplification of the beta-amylase gene in different clones was performed as described before. Table II presents the enzymatic activity in the original strain compared to that in the three clones: this activity was recovered either from the phage lysate or by the method of osmotic shock described in Example II.

TABLE II

EXTRACELLULAR AND CELL-BOUND beta-AMYLASE ACTIVITY IN B. cereus AND IN THE RECOMBINANT CLONES

|  | Extracellular Activity, Unit/Liter | % | Cell-Bound[a] Activity, Unit/Liter | % | Total Activity, Unit/Liter |
|---|---|---|---|---|---|
| B. cereus[b] ATCC 31102 | 1,420 |  | Not determined |  | 1,420 |
| Lambda NM 781 beta Amy 1 | 80 | — | — | — | 80 |
| E. coli CL7004 (pCP 3)[c] | 59 | 77.2 | 17.4 | 22.8 | 76.4 |
| E. coli CL7005 (lambda beta Amy 1)[d] | 19 | 44.2 | 24 | 55.8 | 43 |

[a]Cell-bound activity: treatment with lysozyme with lysis of the cells.
[b]The culture was done at 30° C. overnight (yeast-extract, 1%; bactotryptone, 1%; NaCl, 0.5%).
[c]Overnight cultures at 37° C. (same culture medium composition).
[d]Cultivation at 32° C. → 45° C. → 37° C., activity measured in the supernatant and in the cells after lysis, as for E. coli lambda alpha Amy 1 in Example II.

EXAMPLE IV

Cloning of a Pullulanase Gene

The donor microorganism was a strain of K. pneumoniae described by H. Bender in Biochem. Z., 334. pp. 79–95 (1961) and deposited with the ATCC on June 6, 1963, as No. 15050. It is also mentioned in British Pat. No. 1,273,789 of A. E. Staley.

2.25 μg of donor DNA were extracted and fragmented with Eco RI, using standard conditions, and 1.25 μg of lambda NM781 DNA was cut by the same enzyme, under the same conditions. The incubation was conducted for 3 hours at 37° C., after which the reaction was stopped by heating for 10 minutes at 75° C. The completeness of the restriction was determined as in Example II.

The restricted DNA's were ligated, recovered, and used to infect strain HB101 of E. coli, all as in Example II. About $2 \times 10^5$ PFU were obtained per μg of lambda DNA.

After 2 days' incubation at 37° C. on plates containing BBL Trypticase (a pancreatic digest of casein available from the Baltimore Biochemical Labs., Baltimore, Md.) plus 0.25% pullulan, some plaques showed pullulanase activity, that is to say they were surrounded by opaque rings characteristic of "overgrowing" bacteria. The proportion of pullulanase-producing phages was in the order of 1/2,500.

One was selected and is designated by us as lambda NM781 Pul 1; it was deposited with the NCIB on Apr. 9, 1980, as NCIB No. 11593.

Pullulanase activity was detected by the DNS method and the product of the hydrolysis of pullulan by the phage lysates was identified as maltotriose by thin layer chromatography.

Lambda NM781 Pul 1 contains a large fragment of DNA (from K. pneumoniae) of 13.5 Kb; this fragment was again cleaved by Eco RI leading to two fragments of 6.1 Kb and 7.4 Kb, respectively. The subfragment of 6.1 Kb was then recloned in lambda NM781 and was shown to contain the pullulanase gene. This new recombinant phage is called lambda NM781 Pul 2; it was deposited on Sept. 15, 1980, as NCIB No. 11604.

Figure 5:
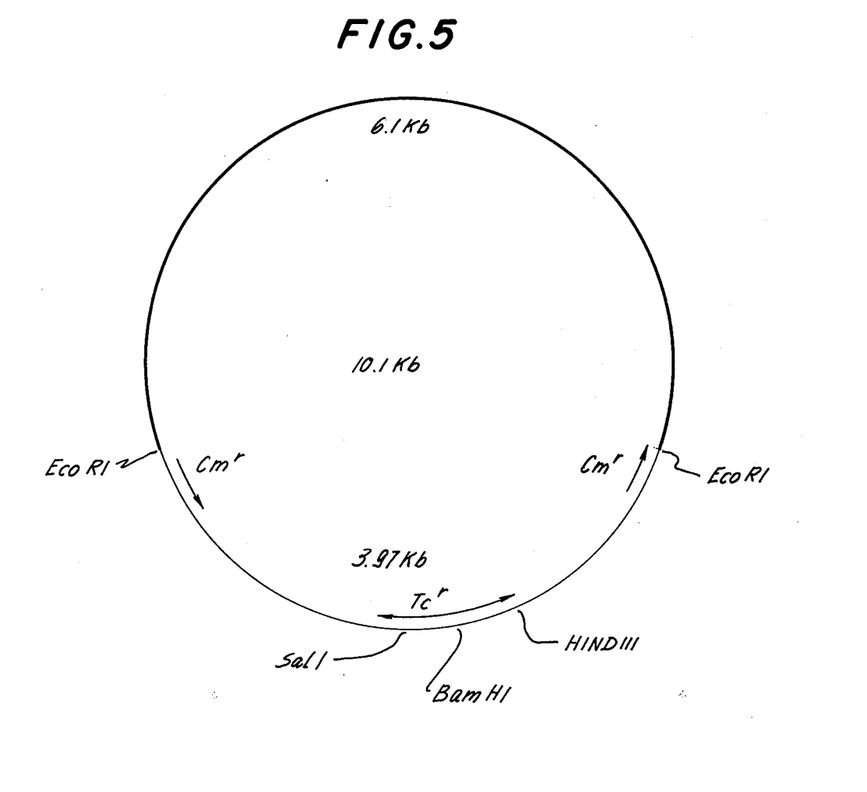
FIG. 5 is a map of the plasmid pCP 4 obtained by inserting a DNA fragment containing a pullulanase coding gene from *K. pneumoniae* (*Klebsiella pneumoniae*) into pACYC184.

The 6.1 Kb subset was further subcloned in the multicopy plasmid pACYC184 (a derivative of pBR322 with the Tc$^r$ gene of the later and a Cm$^r$ gene with one Eco RI site). This new clone is called E. coli CL7006 (pCP 4); it was deposited on Sept. 15, 1980, as NCIB No. 11605. The map of pCP 4 is shown in FIG. 5.

A third subclone was constructed by inserting the 6.1 Kb fragment into phage lambda NM989, as described in Example II. This clone is called E. coli CL7007 (lambda Pul 2); it was deposited on Sept. 15, 1980, as NCIB No. 11606.

The level of expression and the amplification of the pullulanase was studied in all clones. The results are summarized in Table III.

As can be seen from the results, the pullulanase activity is induced by maltose, 0.04% maltose having been added to the LB medium. Furthermore, a Triton X 100 treatment of the membrane fraction was necessary to recover the pullulanase, indicating that the activity is localized in the membranes.

TABLE III

EXPRESSION OF THE Klebsiella PULLULANASE IN E. coli CLONES
The activity is expressed as units of maltose equivalent for a one-liter culture.

|  | Supernatant | Membranes | Total | Enhancement of Enzyme Production |
|---|---|---|---|---|
| Klebsiella pneumoniae + Maltose | 24 | 3.5 | 27.5 | 1 |
| λNM781 Pul 1 | 0.76 | 2.6 | 3.86 | 0.14 |
| λNM781 Pul 1 + Maltose | 2.2 | 9.84 | 12.04 | 0.44 |
| λNM781 Pul 2 | 9.6 | 23.8 | 32.9 | 1.19 |
| λNM781 Pul 2 + Maltose | 8.6 | 26.7 | 35.3 | 1.28 |
| E. coli CL7006 (pCP 4) | Not detected | 3.4 | 3.4 | 0.123[a] |
| E. coli CL7006 (pCP 4) + Maltose[a] | Not detected | 114 | 114 | 4.14[a] |
| E. coli CL7007 (lambda Pul 2) + Maltose[b] | 47 | 93.5 | 140.5 | 5.13[b] |

[a]Overnight cultures.
[b]Cultivation at 32° C. → 45° C. → 37° C., activity measured in the supernatant and in the cells after lysis, as for E. coli lambda alpha Amy 1 in Example II.

Thus, it is apparent that there has been provided, in accordance with the invention, a process for the preparation of recombinant DNA containing genes coding for amylase enzymes, for its incorporation into microorganisms, and for their use to prepare amylases that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. Recombinant DNA containing an amylase or pullulanase gene consisting of a phage selected from the group consisting of NCIB No. 11569, NCIB No. 11572, NCIB No. 11574, NCIB No. 11593, NCIB No. 11604, and mutants thereof.

2. A genetically engineered microorganism characterized in that it comprises a phage containing an amylase or pullulanase gene selected from the group consisting of NCIB No. 11569, NCIB No. 11572, NCIB No. 11574, NCIB No. 11593, NCIB No. 11604, and mutants thereof.

3. A biologically pure culture of a lysogenic strain of E. coli, NCIB No. 11586, characterized in that it carries the recombinant phage, NCIB No. 11572, containing a thermostable alpha-amylase coding gene.

4. A biologically pure culture of a lysogenic strain of E. coli, NCIB No. 11603, characterized in that it carries the recombinant phage, NCIB No. 11574, containing a beta-amylase coding gene.

5. A biologically pure culture of a lysogenic strain of E. coli, NCIB No. 11606, characterized in that it carries the recombinant phage, NCIB No. 11604, containing a pullulanase coding gene.

6. An essentially pure plasmid, having an amylase coding gene, selected from the group: pCP 1 having a molecular weight of approximately 6.56 Kb and a restriction endonuclease cleavage map as shown in FIG. 1, pCP 2 having a molecular weight of approximately 7.67 Kb and a restriction endonuclease cleavage map as shown in FIG. 2, pCP 2.3 having a molecular weight of approximately 4.33 Kb and a restriction endonuclease cleavage map as shown in FIG. 3(b), pCH 1 having a molecular weight of approximately 9.67 Kb and a restriction endonuclease cleavage map as shown in FIG. 3(c), pCP 3 having a molecular weight of approximately 7.61 Kb and a restriction endonuclease cleavage map as shown in FIG. 4, and pCP 4 having a molecular weight of approximately 10.1 Kb and a restriction endonuclease cleavage map as shown in FIG. 5.

7. A biologically pure culture of B. subtilis, NCIB No. 11629, characterized in that its cells contain the plasmid, pCH 1, and that it will grow in a medium containing 20 µg of chloramphenicol per ml of medium producing alpha-amylase enzyme which is excreted into the medium.

8. A biologically pure culture of E. coli, NCIB No. 11570, characterized in that its cells contain the plasmid, pCP 1, that it will grow in a medium containing ampicillin and that it will produce an alpha-amylase enzyme.

9. A biologically pure culture of E. coli, NCIB No. 11573, characterized in that its cells contain the plasmid, pCP 2, that it will grow in a medium containing ampicillin and that it will produce a thermostable alpha-amylase enzyme.

10. A biologically pure culture of E. coli, NCIB No. 11602, characterized in that its cells contain the plasmid, pCP 3, that it will grow in a medium containing ampicillin and that it will produce a beta-amylase enzyme.

11. A biologically pure culture of E. coli, NCIB No. 11605, characterized in that its cells contain the plasmid, pCP 4, that it will grow in a medium containing chloramphenicol and that it will produce a pullulanase enzyme.

* * * * *